United States Patent [19]
Homa

[11] Patent Number: 5,411,496
[45] Date of Patent: May 2, 1995

[54] OSTOMY POUCH CONTAINING BREAKABLE BUBBLES CONTAINING A DEODORIZER

[76] Inventor: Joseph Homa, 137-01A 68th Dr., Flushing, N.Y. 11367

[21] Appl. No.: 203,391

[22] Filed: Mar. 1, 1994

[51] Int. Cl.⁶ .............................................. A61F 5/44
[52] U.S. Cl. .................................... 604/333; 422/5; 424/408
[58] Field of Search ..................... 422/5, 120; 424/400, 424/411, 408; 604/331-333, 336

[56] References Cited

U.S. PATENT DOCUMENTS

| | | | |
|---|---|---|---|
| 3,312,221 | 4/1967 | Overment | 604/333 |
| 3,385,298 | 5/1968 | Fenton | 604/332 |
| 4,496,357 | 1/1985 | Osburn | 604/336 |
| 4,917,692 | 4/1990 | Steer et al. | 604/332 |
| 5,110,597 | 5/1992 | Wong et al. | 424/438 |

*Primary Examiner*—Jerome L. Kruter
*Attorney, Agent, or Firm*—Michael I. Kroll

[57] ABSTRACT

The present invention relates to an ostomy pouch containing breakable deodorizing bubbles therein to facilitate the addition of deodorant when the pouch is reused.

6 Claims, 1 Drawing Sheet

U.S. Patent  May 2, 1995  5,411,496
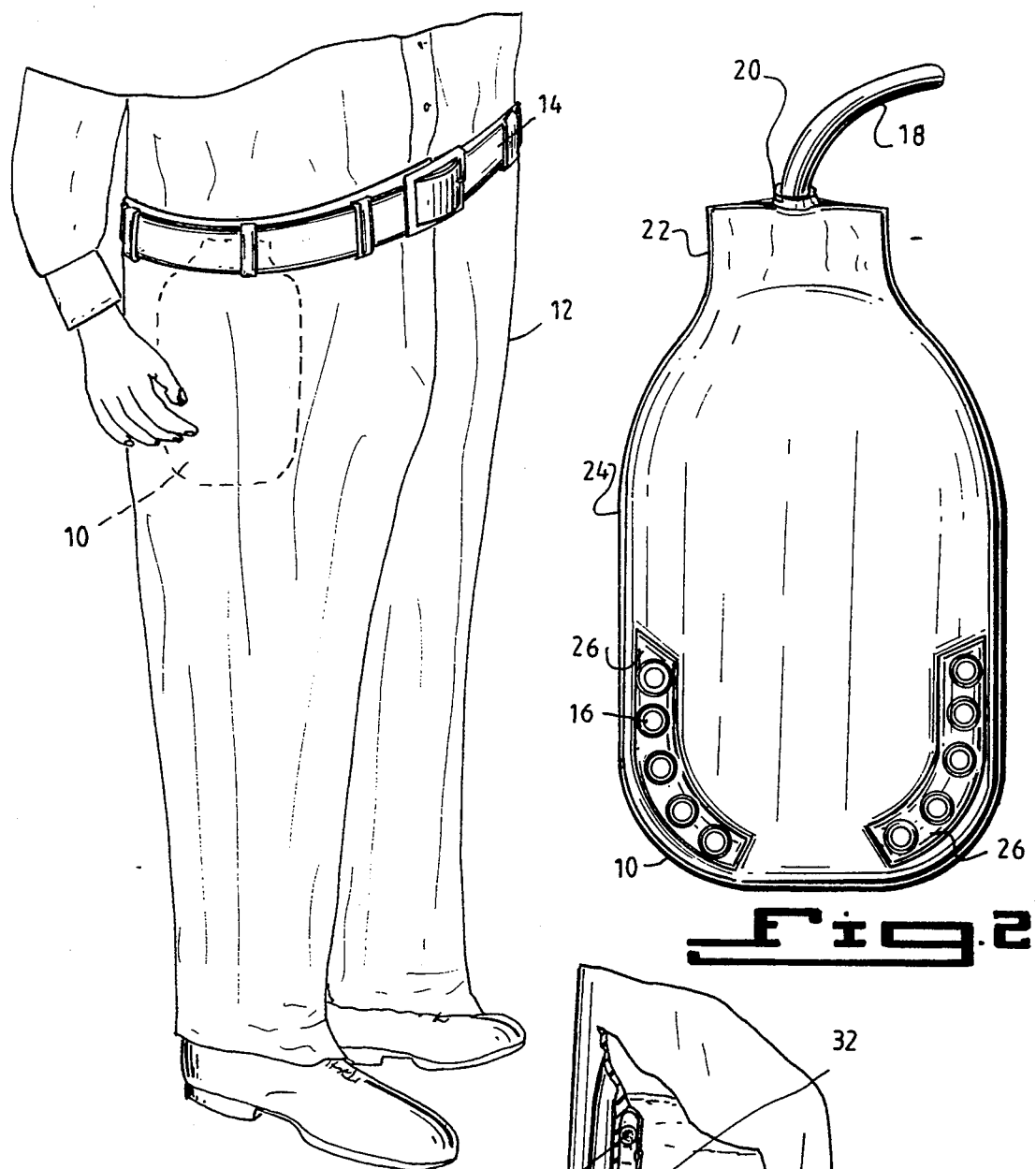

OSTOMY POUCH CONTAINING BREAKABLE BUBBLES CONTAINING A DEODORIZER

BACKGROUND OF THE INVENTION

1. Field of the Invention

The present invention relates to a for an ileostomy bag, a colostomy bag or the like. This bag includes a deodorizing means which is self contained and easily dispersed into the bag to enable reuse.

This invention relates to a colostomy bag, more particularly, to a bag that is adapted to house body fluids and waste matter and thereby dispersing deodorizer into said bag.

2. Description of the Prior Art

In the treatment of human diseases and ailments, it is sometimes necessary to form an opening in the patient's anatomy and to maintain that opening for an indefinite period of time. For instance, diseases involving different parts of the gastro-intestinal and urinary tract can result in a patient being left with an abdominal stoma. The three most common types of abdominal stomas are the colostomy, the ileostomy and the ileal conduit. In the case of an ileostomy, ileal conduit and many colostomy operations, the patient is unable to control the passage of bodily waste material and must rely upon an appliance attached to the body to collect this material.

Various appliances have been proposed in the prior art. A majority of these appliances involve the use of deodorant gels, tablets and liquids or other deodorizing materials which must be placed within the ostomy bag. However, these materials are often messy to apply and are often inadequate to prevent odors. For instance, if a user perspires, such as after exercise or on a hot day, these deodorizing materials are often ineffective in providing a complete deodorizing effect.

Further, many of the prior art arrangements are rather complicated to operate because they require a user to assemble various components or open the ostomy bag and insert the deodorizer. Thus, the user tends to avoid changing the ileostomy or colostomy bag and bacterial infections or other problems may arise. Further, as a complicated sealing arrangement is required, it is often difficult for the bag to be properly attached to the multi-piece connector and leaks may therefore arise.

Furthermore, such complicated deodorizing arrangements may be time consuming and may be difficult for certain users, such as elderly, handicapped or impaired persons or those with arthritis, to use. Over time, prior art constructions are subject to wear. Due to their constructions, this wear can result in leaking of the prior art connectors. Furthermore, the manufacturing cost for these prior art devices tend to rise because of the need for manufacturing and packaging of several different components.

Accordingly, a need exists in the art for a simple and effective bag deodorizing system which is self-contained and easy to operate, which avoids the opening and addition of deodorants without having to carry said deodorants on oneself for application within said ostomy bag.

The prior art teaches a variety of colostomy appliances, for example, as disclosed in U.S. Pat. Nos.: 2,546,779; 2,679,248; 2,684,675; 2,814,295; 2,896,625; 3,125,093; 3,695,268; 3,805,789; 3,826,262; and others. None of the foregoing, nor the prior art described below however, provide for a simple yet effective means of dispersing deodorant into a ostomy pouch for reuse of same hence, eliminating odor.

U.S. Pat. No. 5,098,420

One-piece ileostomy or colostomy bag connector

Daniel J. Iacone

A one-piece bag connector for an ileostomy bag, colostomy bag or the like comprises an annular body portion, lip portion and a belt attachment. The body portion is adapted to surround a stoma of a user and the lip portion is connectable to a bag such that material may be discharged from the stoma to the bag without leakage. The body portion is made of resilient material and directly contacts the user thus avoiding the use of any gels or adhesive materials. The belt attachment connects a belt to the body portion such that a slight pressure is exerted against the user. This pressure plus the resilient nature of the body portion assures a proper seal between the user and the bag connector. Further, an easily attachable detachable snap or screw connection is provided between the lip portion and the bag to assure a proper seal as well as convenience and ease in changing and/or removing the bag. The annular body portion, lip portion and belt attachment can be molded from plastic or the like to form the one-piece connector.

U.S. Pat. No. 4,085,752

Colostomy bag pad

James Canale

A colostomy bag pad that is adapted to be interposed between the bag and the external surface of the abdominal wall and provides an aperture for communication with the external projection of the stoma.

Numerous innovations for drafting devices have been provided in the prior art that are adapted to be used. Even though these innovations may be suitable for the specific individual purposes to which they address, they would not be suitable for the purposes of the present invention as heretofore described.

SUMMARY OF THE INVENTION

Accordingly, it is the primary object of the present invention to Provide a two-piece bag deodorizing means which is simple to use and which provides an effective elimination of odors. When the person releases a bowl movement, in order to reduce the odor, the person must use some form of odor eliminator liquid or tablets which must be introduced into the pouch or they require to take chewable Bismuth Subgallate tablets. Emptying the pouches is a difficult procedure. First the person must remove a clamp from the pouch, then empty and clean the pouch and hence, the person must place odor control tablets or liquid into the pouch. For this reason the person must hold the pouch upside down and with one hand then apply the odor control tablets or liquid with the other hand. The present invention revolutionizes the odor control in a very simple way. The deodorizing material is contained within multiple breakable bubbles. When the person wants to release the deodorant he or she simply pops one of the deodorant containing bubbles.

It is a further object of the present invention to provide an improved two-piece bag deodorizing system which can be placed within said bag for easy addition of deodorant to said bag.

It is yet another object of the present invention to provide a bag connector which is of two-piece construction with deodorizing means, thereby avoiding the need for complicated assembly by the user and avoiding the possibility of losing any of the various parts making up the deodorizer.

A further object of the present invention is to provide a deodorizing system which is sturdier and less prone to wear than found in the prior art.

It is another object of the present invention to provide a deodorizing system which does not require the use of deodorants which must be carried externally to said bag and addition to said bag provides a leak-proof seal.

It is yet a further object of the present invention to provide a deodorizing system which may be worn by a user beneath his or her clothing and yet will be undetectable.

It is still another object of the present invention to provide a one-piece bag connector which permits its user to be active without the fear of developing a leak.

Yet another object of the present invention is to provide a deodorizing system which may be designed to fit a variety of sizes and shapes of people having different sized stomas, including infants and obese people.

It is still another object of the present invention to provide a deodorizing system which is easily used by arthritic, handicapped or impaired users.

Still another object of the present invention is to provide a deodorizing system which is inexpensive and simple to manufacture and which is easier to package than a deodorizing system having many components.

Another object of the present invention is to provide a deodorizing system which requires limited or no maintenance.

It is accordingly an object of the instant invention to provide for a new and improved colostomy bag deodorizing system.

It is another object of the invention to provide for the same at relatively little cost thereby making it generally available.

It is a further object to provide for a deodorizing system that is easily and simply applied.

These and other objects of the present invention are fulfilled by providing a deodorizing system for deodorizing an ostomy bag about a stoma of a user. This deodorizing system includes an bubble-like deodorant containing means which is easily dispersed into the ostomy bag.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in art from this detailed description.

The novel features which are considered characteristic for the invention are set forth in the appended claims. The invention itself, however, both as to its construction and its method of operation, together with additional objects and advantages thereof, will be best understood from the following description of the specific embodiments when read and understood in connection with the accompanying drawing.

BRIEF DESCRIPTION OF THE DRAWING

FIG. 1 is a perspective view of a person having an ostomy pouch contained under his clothing.

FIG. 2 is a cross sectional view of an ostomy pouch exhibiting the deodorizing containing bubbles which are sealed within a retainer.

FIG. 3 is a cross sectional enlarged view of a portion of an ostomy pouch exhibiting the release of deodorant into the pouch to eliminate odor and reuse.

LIST OF REFERENCE NUMERALS UTILIZED IN THE DRAWING

10—OSTOMY POUCH
12—PANTS
14—BELT
16—DEODORANT BUBBLES
18—HOSE
20—POUCH OUTLET PORT
22—POUCH TOP
24—SEAL
26—BUBBLE RETAINER
28—BUBBLE RETAINER SEAL
30—INNER POUCH LAYER
32—DEODORANT
34—OUTER POUCH LAYER

DETAILED DESCRIPTION OF THE PREFERRED EMBODIMENT

Referring to FIG. 1 there is shown an ostomy bag 10 for the collection of bodily excretion fluids and solid waste materials which is concealed under a person's pants 12 held in place by a belt. In the treatment of human diseases and ailments, it is sometimes necessary to form an opening in the patient's anatomy and to maintain that opening for an indefinite period of time. For instance, diseases involving different parts of the gastro-intestinal and urinary tract can result in a patient being left with an abdominal stoma. The three most common types of abdominal stomas are the colostomy, the ileostomy and the ileal conduit. In the case of an ileostomy, ileal conduit and many colostomy operations, the patient is unable to control the passage of bodily waste material and must rely upon an appliance attached to the body to collect this material.

Referring now to FIG. 2 which is a cross sectional view of an ostomy bag 10 having deodorizing bubbles 16 containing deodorant. These multiple deodorizing bubbles are capable of being popped by applying pressure with fingers on both sides of the bag with the bubble in between the fingers. Since, the bubbles are located within the ostomy pouch 10 between the inner 30 and outer 34 layers of the ostomy pouch 10, the deodorant is easily released within the ostomy bag to eliminate emission of odors. When the person releases a bowl movement, in order to reduce the odor, the person must use some form of odor eliminator liquid or tablets which must be introduced into the pouch 10 or they require to take chewable Bismuth Subgallate tablets. Emptying the pouches 10 is a difficult procedure. First the person must remove a clamp from the pouch 10, then empty and clean the pouch and hence, the person must place odor control tablets or liquid into the pouch. For this reason the person must hold the pouch upside down and with one hand then apply the odor control tablets or liquid with the other hand. The present invention revolutionizes the odor control in a very simple way. The deodorizing material 32 is contained within multiple breakable bubbles 16. When the person wants to release the deodorant 32 he or she simply pops one of the deodorant containing bubbles 16.

The deodorizing bubbles 16 are contained within a bubble retainer 26 having which affixes the deodorizing bubbles 16 to either the inner 30 or outer 34 layers of the ostomy bag 10. The ostomy bag 10 has a narrowing top portion 22 and a circumferential seal 24. The top portion 22 may have a pouch outlet port 20 which is connected and sealed to a hose-like structure 18 enabling the device to eliminate liquid bodily waste from the solid bodily waste.

Lastly, referring to FIG. 3 which is a cross sectional enlarged view of a ostomy pouch 10 exhibiting the inner 30 and outer 34 layers of the ostomy pouch 10. The inner 30 and outer 34 layers of the ostomy pouch 10 are circumfrentailly sealed 24, thus, preventing the leaking of bodily excretions. As is depicted in FIG. 3, when the deodorizing bubble 16 is broken, the deodorant 32 is released into the pouch 10 between the inner 30 and outer 34 layers. Therefore, the elimination of odor occurs.

The deodorant contained within bubbles 16 my be in the form of fluid, a gel, a powder, or a tablet.

It will be understood that each of the elements described above, or two or more together, may also find a useful application in other types of constructions differing from the type described above.

While the invention has been illustrated and described as embodied in a ostomy pouch with deodorizing system, it is not intended to be limited to the details shown, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

I claim:

1. An ostomy pouch for wearing by a person for the collection of bodily waste comprising:
    a) an inner and outer layer which is circumferentially sealed to prevent the leaking of bodily waste during excretion,
    b) means for attaching said pouch to a person to collect said bodily waste,
    c) breakable bubble means containing deodorant which is affixed to an inside portion of said inner and outer layer capable of releasing said deodorant to an inside portion of said ostomy pouch to eliminate odors upon squeezing of said bubble means by said person, and
    d) bubble retaining means for supporting, locating and restraining said bubble means within said pouch in a manner to permit said bubble means to be squeezed by said person when deodorant is to be released.

2. An ostomy pouch as described in claim 1, whereas said deodorant is a fluid.

3. An ostomy pouch as described in claim 1, whereas said deodorant is a gel.

4. An ostomy pouch as described in claim 1, whereas said deodorant is a powder.

5. An ostomy pouch as described in claim 1, whereas said deodorant is a tablet.

6. An ostomy pouch as described in claim 1, whereas said bubble means includes multiple breakable bubbles.

* * * * *